United States Patent [19]

Scheibengraber

[11] Patent Number: 5,038,260
[45] Date of Patent: Aug. 6, 1991

[54] GENERATOR FOR GENERATING ONE OR MORE DOTS OR LINES OF LIGHT

[75] Inventor: Karl J. Scheibengraber, Milwaukee, Wis.

[73] Assignee: Charles Lescrenier, Wauwatosa, Wis.

[21] Appl. No.: 360,824

[22] Filed: May 31, 1989

[51] Int. Cl.$^5$ .............................................. F21V 13/04
[52] U.S. Cl. .................... 362/268; 362/296; 362/308; 362/327; 362/341
[58] Field of Search .............. 362/296, 341, 347, 326, 362/327, 328, 308, 268; 350/574

[56] References Cited

U.S. PATENT DOCUMENTS 4,337,502  6/1982  Lescrenier ..................... 362/308
4,674,011  6/1987  Patton et al. .................. 362/328

FOREIGN PATENT DOCUMENTS 125420  11/1931  Austria ........................... 362/268

OTHER PUBLICATIONS

Materials relating to a presentation given at the Conference on Lasers and Electro-Optics on May 21-25, 1985 in Baltimore, Md., by the inventor identified in the present application.

Primary Examiner—Ira S. Lazarus
Assistant Examiner—Sue Hagarman
Attorney, Agent, or Firm—Andrus, Sceales, Starke & Sawall

[57] ABSTRACT

A light beam generator provides a thin ray or plane of light of high intensity with a non-laser light source. Light emanating from a light source such as a quartz-halogen bulb is applied to a convex reflector or negative lens to demagnify the image of the light producing element. The demagnified image is passed through a refracting means such as convex lens to form a thin ray or plane of light. The reflective or refractive elements can be spherical or cylindrical depending on whether a dot or line of light is desired.

21 Claims, 4 Drawing Sheets

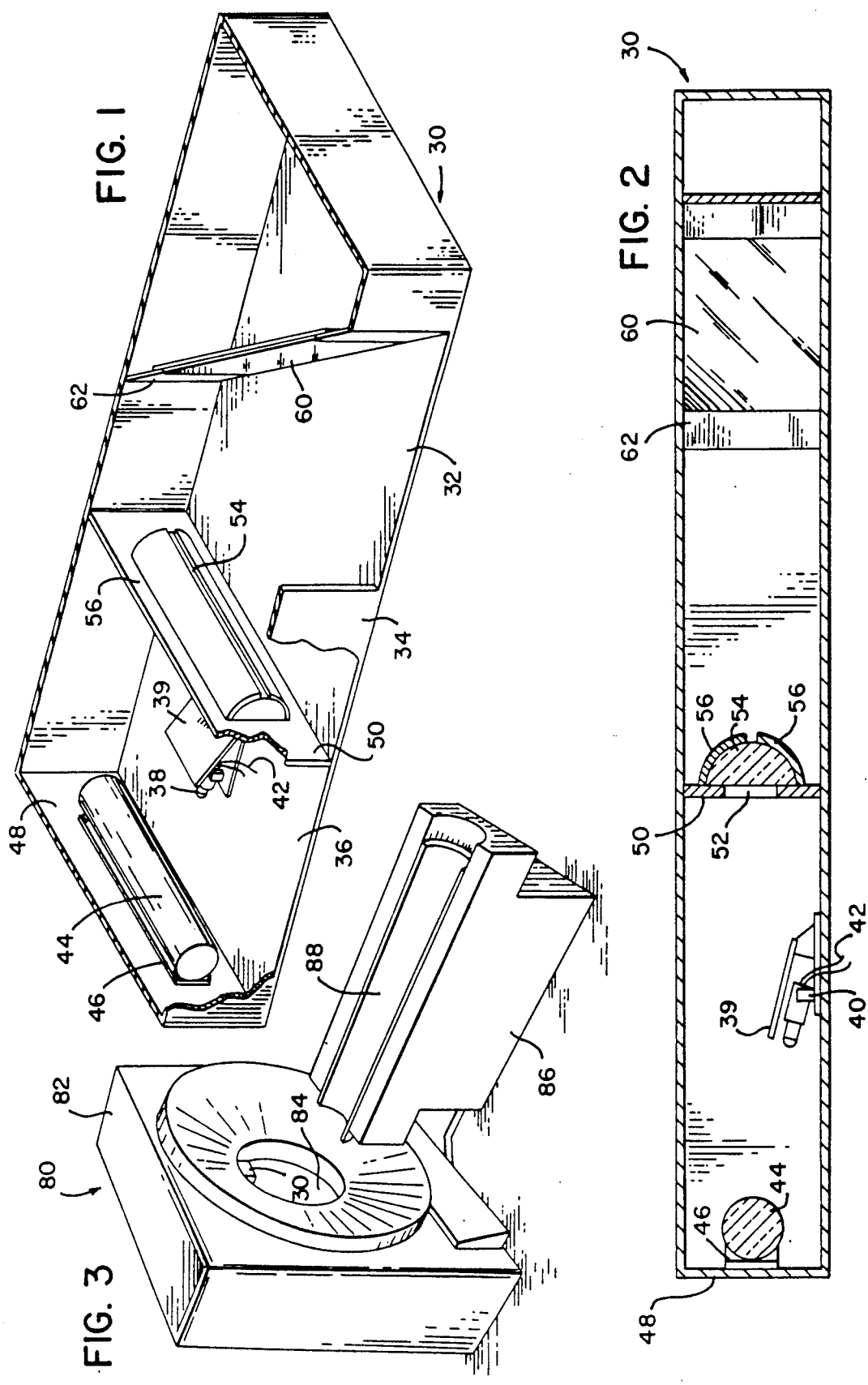

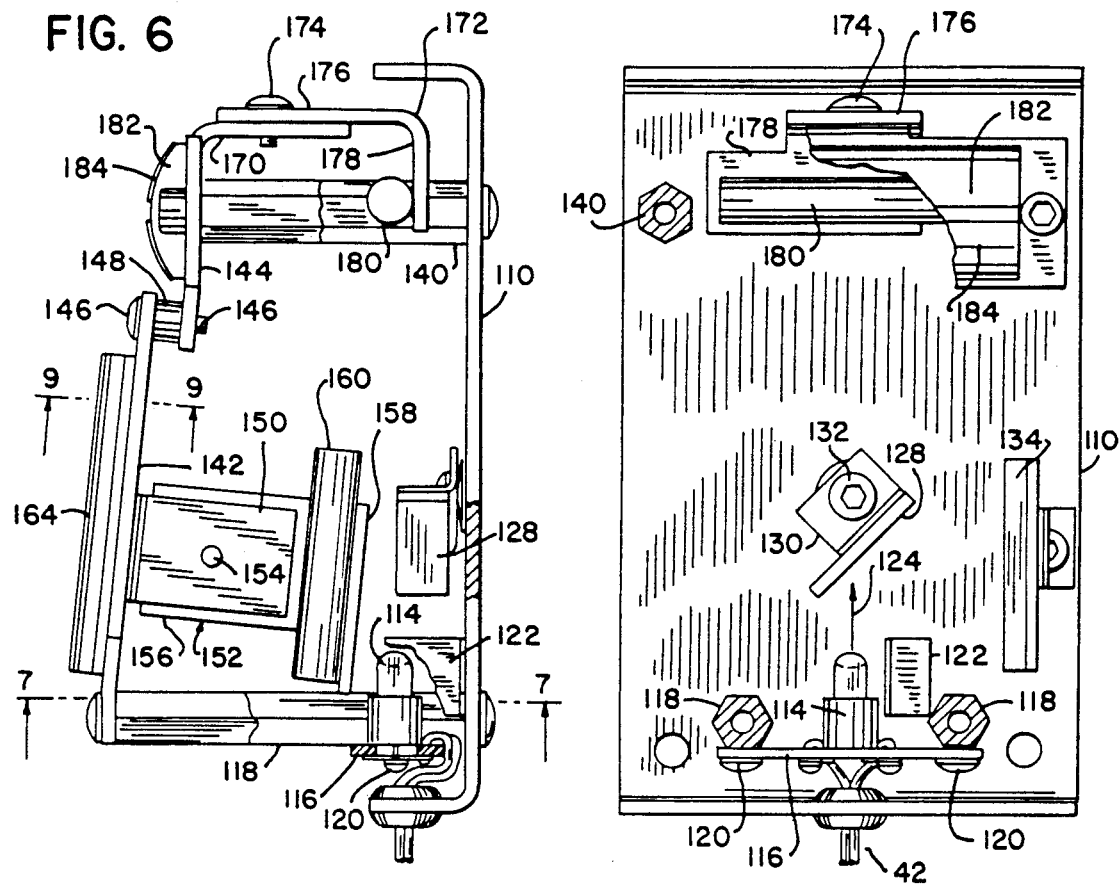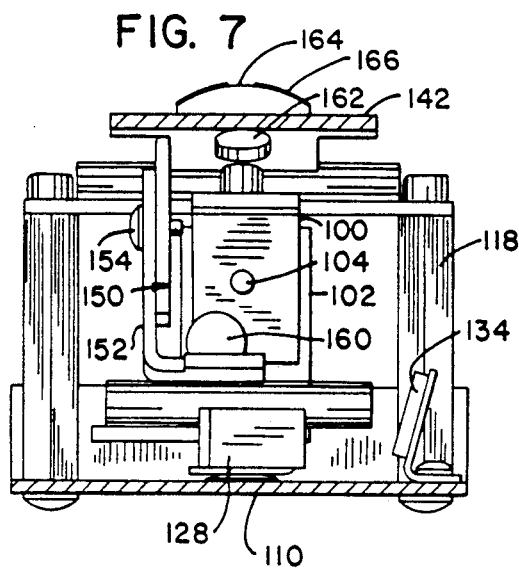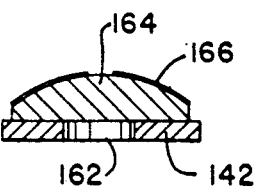

GENERATOR FOR GENERATING ONE OR MORE DOTS OR LINES OF LIGHT

The present invention relates to an improved light beam generator. More particularly, the present invention relates to a generator capable of generating beams of light of generally high intensity but without the need to use a laser or similar light source.

While not limited thereto, the light beam generator of the present invention may find use in the field of radiological medical equipment. A patient must be accurately positioned with respect to the radiation beam of such equipment in order to achieve the desired degree of effectiveness in diagnosis or therapy while minimizing undesirable side effects. Since the radiation beam is not visible to the eye, some means must be provided to identify and locate the beam and insure that it will impinge on the correct portion of the patient. For this purpose, a reference light pattern bearing a predetermined relationship to the radiation beam may be generated. As the patient is oriented with respect to the radiation beam, a pattern of light is applied to the patient and used to properly position the patient with respect to the radiation beam. When the light is in the form of a ray, a dot of light is formed on the patient when the light is so applied. When the light is in the form of a plane, a line of light is formed on the patient.

In radiological equipment of the axial tomographic imaging type, a plane of light may be generated to lie in the imaging plane of the equipment. When the patient is positioned in the equipment, a line will appear on the patient indicative of the imaging plane. The radiologist can thus easily identify the plane that will be imaged in a subsequent scanning operation.

Planes or dots of light may also be utilized to indicate the boundaries or extent of a conventional radiological beam. For example, planes of light may be arranged in a cross to indicate the central axis of a radiological beam. A rectangle of planes or a plurality of dots may be employed to mark the extent of the beam established by an x-ray collimator.

U.S. Pat. Nos. 4,730,895, 4,337,502 and 4,242,587 to the same assignee as the present application show various types of alignment systems utilizing beams of light.

When used for the above described purposes, it is preferable that the planes of light be narrow in width and that the dots be small in order to insure accurate alignment or positioning. It is further desirable that the beams of light be sufficiently bright so that the lines or dots created thereby can be easily observed under ambient lighting conditions.

Heretofore, laser light sources have frequently been used in light beam generators in order to obtain sufficient brightness, narrowness, and depth of field in the lines or dots. While possessing the advantages of intensity and low divergence, the use of laser light sources is attended by a number of disadvantages. Laser light sources, such as those of the helium-neon type, are rather bulky devices. This may hinder or prevent their positioning at the appropriate location in the radiological equipment, for example, within a computerized axial tomographic x-ray machine. Laser light sources also tend to be rather expensive. Laser light sources, such as He-Ne lasers that produce visible light, require excitation by potentially lethal voltages which are undesirable in any case and particularly in a medical diagnosis or treatment environment.

It is, therefore, the object of the present invention to provide an improved light beam generator that is capable of providing light beams of high intensity, narrowness, and sufficient depth of field without employing a laser light source. The advantages of a laser light source are thus retained while the disadvantages are lessened or eliminated.

The unique construction of the present invention permits the use of low cost light sources, such as quartz-halogen incandescent light bulbs or light emitting diodes of the ultra bright type as the light source.

Briefly, the light beam generator of the present invention employs a small light source or a light source having a small light emitting element of the above type. The image of the light emitting element of the light source, such as the filament, is demagnified, as by a convex mirror or negative lens. A refracting means, such as a convex lens of the cylindrical or spherical type, forms the demagnified image into a bright beam of low divergence. The lens may be stopped down to assist in forming the beam.

The invention will be further understood by reference to the following detailed description of preferred embodiments, taken in conjunction with the drawing.

In the drawing,

FIG. 1 is a perspective view of a light beam generator of the present invention suitable for generating a plane of light;

FIG. 2 is a cross-sectional view of the light beam generator shown in FIG. 1;

FIG. 3 is a perspective view of radiological equipment of the computerized axial tomographic type with which the present invention may be utilized;

FIG. 6 is a side view of the light beam generator taken from the right-hand side when viewed as in FIG. 5, portions of the view being broken away;

FIG. 7 is a view taken along the line 7—7 of FIG. 6;

FIG. 8 is a top view of the light beam generator of FIG. 4 with portions thereof broken away;

FIG. 9 is a cross sectional view through a cylindrical lens element employed in the light beam generator of the present invention taken along the line 9—9 of FIG. 6;

Figure 10:
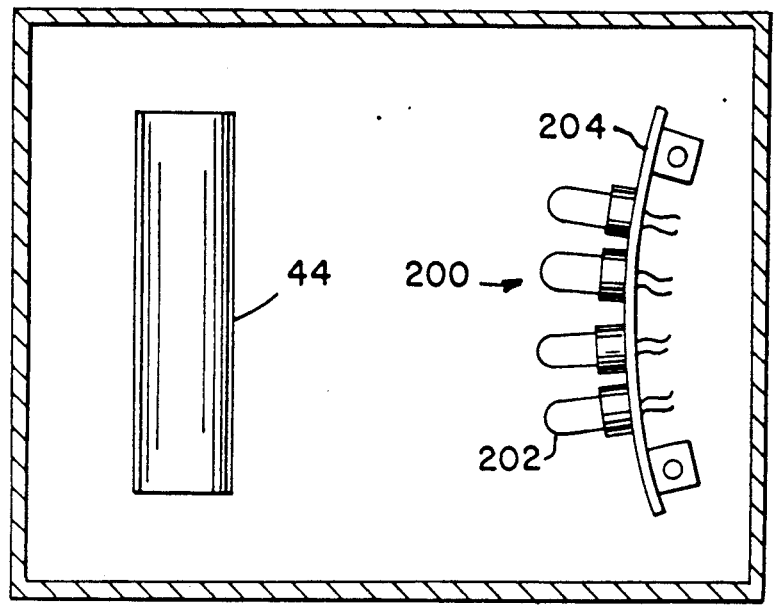
Figure 11:
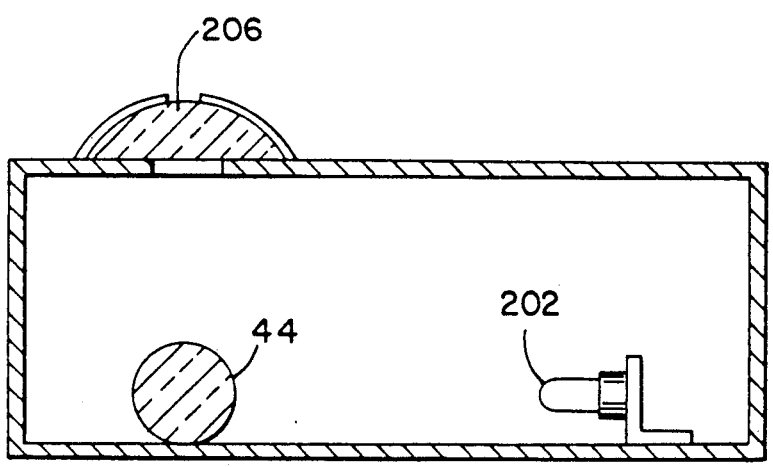
Figure 12:
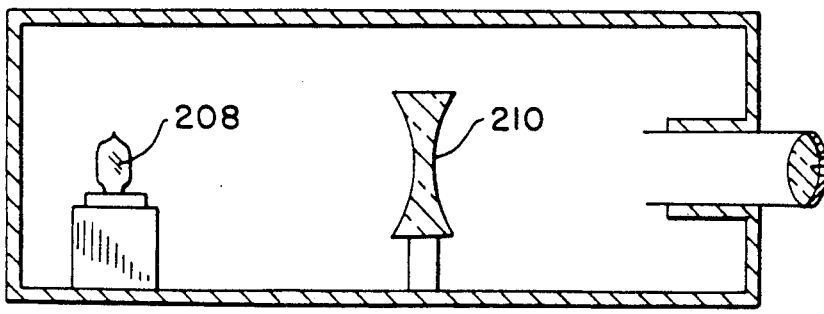

FIG. 10 is a horizontal cross sectional view of another embodiment of the light beam generator of the present invention showing use of a different type of light source; and FIG. 11 is a vertical cross sectional view through the embodiment of the light beam generator shown in FIG. 10; and FIG. 12 is a vertical cross sectional view through yet another embodiment of the light beam generator of the present invention.

As shown in FIG. 1, light beam generator 30 of the present invention is provided with window 32 through which a plane of light may emerge.

Light beam generator 30 includes housing 34 having base member 36. A light source 38 is secured to base member 36 by bracket 40, shown in FIG. 2. Light source 38 may be a small bulb of the incandescent quartz-halogen type. For example, light source 38 may be the quartz-halogen light bulb sold by Welch Allyn under the designation #01075. It would also be possible to utilize a light emitting diode for the light source. For example, the light emitting diode manufactured and sold by Stanley under the designation H-3000 would be suitable for use as light source 38. A xenon tube or other suitably bright, incoherent light source can also be utilized. The light source may also comprise the light emitting end of an optical fiber.

Light source 38 is connected to an appropriate power supply. The power supply may include a transformer that steps down power mains voltage, such as 110 volts AC, to a lower, safer voltage, such as 5-6 volts. A similar low-voltage power supply may be used for a diode light source. In either event, the high voltage power supplies heretofore required by lasers are avoided.

The light emitting element in light source 38 of the incandescent type is a coiled filament. The light bulb includes an integral lens in the end of the bulb that focuses the light emanating from the coiled filament.

Light shield 39 may be mounted behind light source 38.

The light output of light source 38, and particularly that from the coiled filament is applied to small diameter, convex cylindrical mirror 44 mounted on bracket 46 on end wall 48 of housing 34. Cylindrical mirror 44 diverges the light from light source 38 in the well known manner of a convex mirror. This divergence gives the appearance of a small point light source resulting in a demagnification or reduction in the image of the coiled filament from light source 38. Mirror 44 may be formed of a silvered glass rod, or the like. A portion of the cylindrical mirror 44 may be flattened to assist in affixing the mirror to bracket 46.

Plate 50, parallel to end wall 48, is mounted in housing 34 on the opposite side of light source 38 from mirror 44. As best shown in FIG. 2, plate 50 contains slot 52. A plano convex cylindrical lens 54 is mounted on plate 50 over slot 52 to receive the light from cylindrical mirror 44 passing through slot 52. The plano convex lens focuses the diverged light from cylindrical mirror 44, forms same into a plane of light, and collimates or renders the rays of light emitted by lens 54 substantially parallel. The side portions of lens 54 may be rendered opaque by coating 56 to stop down the lens and leave a small central slit in the center thereof The action of lens 54 and the stopping down of lens 54 by aperture 52 and coatings 56 increases the depth of field of the line of light generated by lens 54. The action of lens 54 is thus one of generating a high intensity, narrow beam of light with very small divergence.

Mirror 60 is mounted on plate 62 set at a 45° angle with respect to plate 50. Mirror 60 receives the light emitted by lens 54 and directs a high intensity thin plane of light out window 32 parallel to base 36.

The intensity and thinness of the plane of light generated by light source 30 arises from the use of the small filament image of high intensity light source 38, the demagnification of the light source image by convex cylindrical mirror 40, and the focusing of the demagnified filament image into a narrow line by stopped-down plano convex cylindrical lens 54.

It will be appreciated that if a ray of light, rather than a plane of light, was desired, cylindrical mirror 44 could be replaced with a spherical mirror and a spherical lens used instead of a cylindrical lens. Or, a plano-convex cylindrical lens, such as lens 54, could continue to be used with a spherical mirror to generate a line of light.

FIG. 3 shows a typical application for the light source 30 of the present invention in computerized axial tomographic x-ray machine 80. X-ray machine 80 has gantry 82 containing the x-ray generators and receptors arranged about a central opening 84. The x-ray images produced by machine 80 are resolved in a vertical plane.

X-ray machine 80 also contains patient support 86 containing cradle 88. When the patient is to be examined, he/she is placed on cradle 88 and advanced into opening 84 of gantry 82.

Light beam generator 30 of the present invention may be employed to generate a vertical plane corresponding to the imaging plane of machine 80. If desired, another light beam generator 30 may be employed to generate a plane of light normal to the imaging plane that shows the center line of opening 84. A cross of light would then appear on the patient when positioned within gantry 82.

Figures 4, 5:
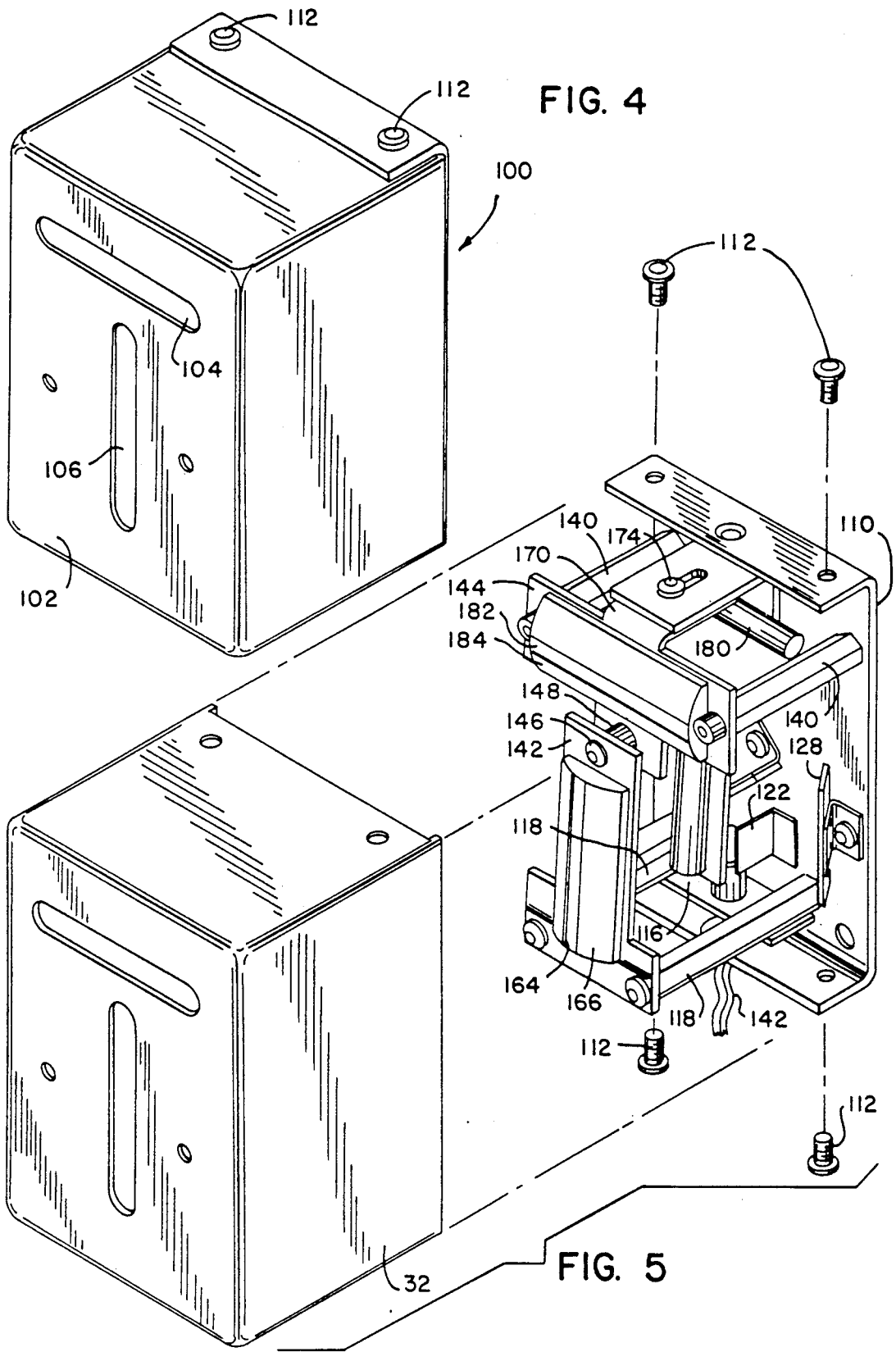
FIG. 4 is a perspective view of a light beam generator of the present invention suitable for generating crossed planes of light.
FIG. 5 is a view of the light beam generator of FIG. 4 with the cover removed.

Or, a single light beam generator 100 such as that shown in FIG. 4, that generates intersecting planes of light may be employed in gantry 82. Light beam generator 100 includes housing 102. Light beam generator 100 is shown as being of the type that generates two mutually perpendicular, intersecting planes of light. For this purpose, housing 102 has a window 104 that is generally horizontal when light beam generator 100 is oriented as shown in FIG. 4. A generally horizontal plane of light may emerge from the window 104. Housing 102 includes a generally vertical window 106 through which may emerge a generally vertical plane of light. This plane may diverge vertically and may be directed upwardly toward the horizontal plane. The planes of light from windows 104 and 106 will thus intersect in front of light generator 100. When applied to an object, a cross of light lines will be generated on the object. As noted above, the light beam emerging from window 104 may indicate the tomographic plane of radiological equipment 80 while the light beam emerging from window 106 identifies the axis of the equipment and the longitudinal axis of the patient, or vice versa.

As shown in FIG. 4, light beam generator 100 contains base member 110. Housing 102 may be fastened to base member 110 by appropriate fasteners such as screws 112.

As best shown in FIGS. 6 and 7, light source 114 is mounted on base 110 adjacent one end thereof. Bracket 116 may be employed for this purpose. As shown in FIG. 6, light source 114 may be oriented generally parallel to base 110. Bracket 116 may be mounted on posts 118 fixed to base 110 by bolts 120. A light shield 122 is mounted on base 110 adjacent one side of light source 114. Light source 114 may be similar to light source 38.

The light output from the light emitting element in light source 114 is projected generally along axis 124 shown in FIG. 7. Mirror 128 is mounted on bracket 130 that is fastened to base 110 by bolt 132. Mirror 128 lies at an angle of 45° to the axis of projection. Bolt 132 may be loosened to pivot mirror 128 to obtain the desired orientation. As shown most clearly in FIG. 6, the height of mirror 128 above base 110 is such that the upper edge of mirror 128 lies at approximately the center line of light source 114. A portion of the light of light source 114 is thus reflected by mirror 128 and a portion passes over mirror 128 on axis 124.

A second planar mirror 134 is mounted on base 110, as shown in FIGS. 7 and 8 to receive and further reflect the light reflected by mirror 128. The plane of mirror 134 lies parallel to the axis of projection 124 of light source 114. Mirror 134 is tilted with respect to a normal to base 110, as seen in FIGS. 7 and 8.

As noted above, a pair of posts 118 extend from base member 110 adjacent light source 114. A corresponding pair of posts 140 is located at the other end of base member 110.

Posts 118 and 140 mount a pair of small diameter, convex cylindrical mirrors and a pair of plano-convex cylindrical lenses. Plate 142 is mounted on posts 118 to extend from the posts in the direction of axis 124. Plate 142 is coupled to plate 144 mounted on posts 140 by means of bolt 146 that is threaded in a tapped hole in plate 144. Bolt 146 is surrounded by spacer 148.

A flange 150 depends from plate 142. Flange 150 may be integrally formed with plate 142. L-shaped bracket 152 is mounted on flange 150 by bolt 154. Portion 156 of bracket 152 contains a slot through which bolt 154 passes so that bracket 152 may be moved with respect to flange 150 for focusing purposes. Portion 158 of bracket 152 lying normal to portion 156 contains small diameter, convex, cylindrical mirror 160. Mirror 160 receives light reflected off mirrors 128 and 134. A portion of cylindrical mirror 160 may be flattened to assist in affixing the mirror to portion 158.

Plate 142 contains slot 162 (see FIG. 6). A plano convex cylindrical lens 164 is mounted on plate 142 over the slot 162 to receive the light from cylindrical mirror 160 passing through slot 162. The side portions of lens 162 are rendered opaque by coating 166 leaving a small central slit down the center of the lens.

Flange 170 depends from plate 144. Flange 170 may be integrally formed with plate 144. L-shaped bracket 172 is mounted on flange 170 by bolt 174. Portion 176 of bracket 172 contains a slot through which bolt 174 passes so that bracket 172 may be moved with respect to flange 170 for focusing purposes. Portion 178 of bracket 172 lying normal to portion 176 contains small diameter, convex cylindrical mirror 180. Mirror 180 receives light from light source 114 projected along axis 124 and over the top of mirror 128. As with mirror 160, a portion of mirror 180 may be flattened to assist in affixing the mirror to portion 178.

Plate 144 is also slotted. A plano convex cylindrical lens 182 is mounted on plate 144 over the slot to receive the light from cylindrical mirror 180 passing through the slot. The sides of lens 182 are rendered opaque by coating 184 leaving a small central portion in the center of the lens.

In operation, light source 114 is energized by a low voltage source through conductors 42. Light is emitted by light source 114 along axis 124. A portion of the light is reflected off mirror 128 on to mirror 134. The light applied to mirror 134 is, in turn, reflected to convex cylindrical mirror 160. The convex cylindrical surface of mirror 160 reflects a greatly demagnified or reduced image of the light emitting filament in light source 114. The diverged light from mirror 160 is applied to plano convex lens 164. Stopped-down lens 164 focuses the image into a thin plane of light.

The light from light source 114 projected along axis 124 passes over the top of mirror 128 and is applied to cylindrical lens 180. The image of the light producing element in light source 114 is reduced or demagnified by lens 110 and applied to plano convex lens 182 where it is focused into a thin plane.

As can be most clearly seen in FIG. 6, convex cylindrical mirror 160 and plano convex lens 164 lie at an angle to base 110. The plane of light projected from lens 164 is projected toward the plane of light projected from lens 182. This angle of projection, plus the divergence of the plane of light in the vertical plane causes the plane of light projected by lens 164 and the plane of light projected by lens 182 to cross.

The intensity and thinness of the plane of light generated by light beam generator 100 arises from the use of a small filament light source, the demagnification of the light source by convex cylindrical mirrors 160 and 180 and the focusing of the demagnified filament image into a line by stopped-down plano convex cylindrical lenses 164 and 182.

FIGS. 10 and 11 show a light source 200 in the form of a row of light emitting diodes 202 mounted on bracket 204. The light from the row of light emitting diodes may be applied to a small diameter cylindrical mirror, such as mirror 44 along the entire axial length of the mirror for projection through stopped-down lens 206 to facilitate the generation of a plane of light.

In the alternative, a row of light emitting optical fibers or an incandescent light having an elongated filament running parallel to mirror 44 could be employed for a similar purpose.

FIG. 12 shows another embodiment of the present invention in which the image reduction of light source 208 is obtained with negative lens 210. The light bulb comprising light source 208 is oriented so that the side of the filament of the light bulb applies light to lens 210. The light bulb made and sold by the Osram Corp. under the designation W465 or HPR2 is suitable for use as light source 208. Negative lens 210 demagnifies the image of the filament of the light source to increase the divergence of the light rays. Negative lens 210 may be of the "fisheye" type to maximize demagnification. Negative lens 210 is positioned in front of positive, convex lens 212 that forms a ray of light. Lens 212 may be stopped down in the same manner as lens 54, 164, and 182. Lens 212 may be movable toward and away from lens 210 for focusing purposes.

Various modes of carrying out the invention are contemplated as being within the scope of the following claims particularly pointing out and distinctly claiming the subject matter which is regarded as the invention.

I claim:

1. A light beam generator for projecting a high intensity beam of light having a small dimension normal to the direction of projection, said light beam generator comprising:
a non-laser light beam generating means having a small light emitting element;
means for demagnifying the image of said light emitting element of said light beam generating means, said image demagnifying means comprising convex reflecting means; and
a refracting means for receiving said demagnified image and for projecting same into a beam of light having generally parallel rays.

2. The light beam generator according to claim 1 wherein said image demagnifying means comprises convex cylindrical reflecting means.

3. The light beam generator according to claim 2 wherein said cylindrical reflecting means has an axis; wherein said refracting means has a corresponding axis and wherein said axes of said reflecting means and refracting means are parallel.

4. The light beam generator according to claim 2 wherein said light beam generating means has a thin light emitting element extending parallel to the axis of said cylindrical reflecting means.

5. The light beam generator according to claim 1 wherein said refracting means comprises a convex lens.

6. The light beam generator according to claim 5 wherein said refracting means comprises a positive cylindrical lens for generating a plane of light.

7. The light beam generator according to claim 5 wherein said refracting means comprises a plano-convex cylindrical lens for generating a plane of light.

8. The light beam generator according to claim 1 wherein said refracting means comprises a positive spherical lens for generating a ray of light.

9. The light beam generator according to claim 1 wherein portions of said refracting means are opaque to provide a stopped down center slit through which the beam of light may pass.

10. The light beam generator according to claim 1 further including a plane mirror for deflecting light within the generator.

11. The light beam generator according to claim 1 further including a plurality of image demagnifying means and a plurality of refracting means for generating a plurality of beams of light.

12. The light beam generator according to claim 11 further including means for providing a portion of the light from said light source to a first pair of image demagnifying means and refracting means and a portion of said light to a second pair of image demagnifying means and refracting means.

13. The light beam generator according to claim 11 wherein said image demagnifying means and refracting means are so arranged that the projected light beams intersect.

14. The light beam generator according to claim 13 wherein said refracting means comprise plano-convex cylindrical lenses and wherein said light beam generator generates intersecting planes of light.

15. The light beam generator according to claim 1 wherein said light beam generating means comprises an incandescent light source.

16. The light beam generator according to claim 15 wherein said light beam generating means comprises a halogen bulb.

17. The light beam generator according to claim 1 wherein said light beam generating means comprises a light-emitting diode.

18. The light beam generator according to claim 1 wherein said light beam generating means includes fiber optic light guide means.

19. The light beam generator according to claim 1 wherein said light beam generating means comprises a single light source.

20. The light beam generator according to claim 1 wherein said light beam generating means comprises an array of light sources.

21. The light beam generator according to claim 20 wherein said light beam generating means comprises a linear array of light sources.

* * * * *